United States Patent [19]

Kissel et al.

[11] 4,215,148
[45] * Jul. 29, 1980

[54] ACROLEIN BUFFERING COMPOSITION AND METHOD OF ENHANCING EFFECTIVE LIFE OF ACROLEIN IN AN AQUEOUS MEDIUM

[75] Inventors: Charles L. Kissel, Anaheim; Frederick F. Caserio, Jr., Laguna Beach, both of Calif.

[73] Assignee: Magna Corporation, Santa Fe Springs, Calif.

[ * ] Notice: The portion of the term of this patent subsequent to Jul. 29, 1997, has been disclaimed.

[21] Appl. No.: 916,418

[22] Filed: Jun. 16, 1978

[51] Int. Cl.² .............................................. A01N 9/24
[52] U.S. Cl. ...................................... 424/333; 71/66; 71/77
[58] Field of Search ........................................ 424/333

[56] References Cited

U.S. PATENT DOCUMENTS

| | | | |
|---|---|---|---|
| 2,925,315 | 2/1960 | Pasternak | 424/333 |
| 3,250,667 | 5/1966 | Legator | 424/333 |

OTHER PUBLICATIONS

Chemical Abstracts, vol. 84 (1976), p. 63478s.

*Primary Examiner*—Leonard Schenkman
*Attorney, Agent, or Firm*—William C. Norvell, Jr.

[57] ABSTRACT

The life of acrolein in an aqueous medium is increased by incorporation into the aqueous medium of an effective amount of a buffered acid preferably selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

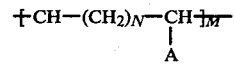

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$.

15 Claims, No Drawings

ACROLEIN BUFFERING COMPOSITION AND METHOD OF ENHANCING EFFECTIVE LIFE OF ACROLEIN IN AN AQUEOUS MEDIUM

CROSS REFERENCE TO RELATED APPLICATION

This application is related in subject matter to copending Application Ser. No. 916,417, filed on even date herewith, and entitled "Acrolein Composition and Method of Enhancing Effective Life Thereof In An Aqueous Medium", Charles L. Kissel and Frederick F. Caserio, Jr., Inventors, and assigned to the same assignee as this application.

BACKGROUND OF THE INVENTION

1. FIELD OF THE INVENTION

The invention relates to a buffered acrolein composition and method of enhancing the lifetime of acrolein in an aqueous medium by incorporation of a buffered organic acid, buffered inorganic acid or combinations thereof to the aqueous medium, and thereby adjusting the pH of the medium to from between about 2 and about 6.

2. DESCRIPTION OF THE PRIOR ART

Acrolein is used in numerous fresh water environments, as well as in brines and salt water, to kill aerobic, anaerobic, and sulfate-reducing bacteria, to remove aquatic weeds and snails, and to destroy algae, fungi, and other undesirable aquatic organisms. Of particular importance is the special use of acrolein in oilfield brines because of its potential biocidal action. This use of acrolein increases the efficiency of oilfield waterflooding and brine disposal operations. Acrolein also is used in oil field operations to scavenge deadly hydrogen sulfide. As the lifetime of acrolein is increased, the number of undesirable organisms destroyed increases, as does the amount of hydrogen sulfide scavenged.

Heretofore, it has been thought that the rate of the decline in acrolein concentration in an aqueous medium will inherently increase as the acid concentration increases and the pH decreases. This rate of decline in acrolein concentration has been reported to conform to the Hammett acidity function. Even the containers bearing commercial acrolein generally carry warning labels recommending that it be kept away from all acids, and particularly, strong acids, such as hydrochloric acid and sulfuric acid.

Acrolein inherently declines in concentration in aqueous media. The period of time between the initial acrolein injection and that time at which the acrolein becomes ineffective as either a biocide, herbicide, or hydrogen sulfide scavenger, is defined as the acrolein lifetime.

It has been found that variables such as temperature and composition of phases present in the aqueous based medium will cause both dilution and effective disappearance of acrolein. Since these aqueous environments generally flow, the acrolein will decline in concentration at considerable distance downstream from the injection point. Increasing the initial injection concentration of acrolein does not significantly alter the distance-time relationship at which the acrolein is depleted to an ineffective level.

One obvious solution involves the usage of multiple injection sites. However, this solution increases the cost of treatments involving acrolein in an arithmetic relationship to the number of injection sites. Additionally, since acrolein is a somewhat difficult material to handle, the multiple injection solution increases the danger of possible environmental accidents.

SUMMARY OF THE INVENTION

It has been discovered that, contrary to previously published statements and beliefs, surprisingly, the lifetime of acrolein can, in fact, be substantially increased by lowering the pH of the aqueous medium containing the acrolein from normal values from between about 7 to about 8, to a range of from between about 2 to about 6, with a preferred or optimum range from between about 3 and about 4. Regardless of the nature of the aqueous medium, the lifetime of acrolein may be increased by actually lowering the pH of the system. Lowering of the pH of the aqueous medium can be accomplished by the addition of a buffered organic or buffered inorganic acid, or combinations thereof, selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

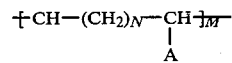

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$.

DESCRIPTION OF THE PREFERRED EMBODIMENTS

Lowering of the pH fo an aqueous medium from about 7 to an acidic value between about 2 and about 6 has been found to substantially increase the lifetime of acrolein. It has been found that the maximum beneficial increase in the lifetime of acrolein is obtained when the pH of the aqueous medium is adjusted to form between about 3 and about 4. However, the exact pH necessary to obtain the optimum enhancement in the lifetime of acrolein is directly dependent upon the physical and chemical characerictics of the particular aqueous medium to be treated. Preferably, the lifetime of acrolein can be further increased at any given pH by using the anion of a strong buffered acid, as opposed to using an anion of a weaker buffered acid. Regardless of the choice of anion, the lifetime of acrolein will be increased at a lower or acidic pH when compared with an equivalent aqueous medium having a neutral pH.

Exemplary of some of the buffered acids which may be utilized in the present invention are acetic acid, benzoic acid, formic acid, phosphoric acid, sulfuric acid, hydrochloric acid, sulfamic acid, and nitric acid. The stronger buffered acids, such as sulfuric, hydrochloric and acetic acid are preferred.

The pH of the aqueous medium may be adjusted to the acid side either prior to or after the desired amount of acrolein is introduced into the medium. Of course, the amount of buffered acid necessary to adjust the aqueous medium to the desired pH level is dependent upon the strength of the selected buffered acid, the composition of the aqueous medium itself, the quantity of acrolein present or to be added to the aqueous medium, and the extension of effective life desired for the acrolein in the aqueous medium. Well known and commercially available techniques and equipment used in determining and monitoring pH levels may be utilized to determine when a sufficient and desired amount of acid material has been introduced into the aqueous medium.

By utilization of the word "buffer" and the terminology "buffered acid" and "buffered acid solution", it is intended to refer to any substance or combination of substances, which, when dissolved in water, produces a solution which resists a change in its hydrogen ion concentration upon the addition of an acid or a base.

A mixture of a weak acid and one of its salts, or of a weak base and a salt with a common ion, maintains a practically constant pH valve upon the addition of an acid or an alkali, or upon dilution. This resistance to change in pH is known as buffering, and a mixture which has this property is called a buffer mixture, or simply a buffer. If a solution contains equivalent quantities of acetic acid and sodium acetate, the addition of hydrogen ion, as from a little hydrochloric acid, for example, will not cause a marked change in the reaction of the solution because the hydrogen ions immediately combine with acetate ions to form undissociated acetic acid: $H^+ + C_2H_3O_2^- \rightleftharpoons HC_2H_3O_2$. The addition of a small quantity of a strong alkali such as sodium hydroxide is at once followed by a reaction with acetic acid to form sodium acetate, and little change in pH occurs.

The quantitative relations may be deduced from the ionization constant in question. The ionization constant of acetic acid is $1.86 \times 10^{-5}$ at 25° C.

$$([H^+][C_2H_3O_2^-]/[HC_2H_3O_2]) = 1.86 \times 10^{-5}.$$

If sodium acetate is added to a solution of acetic acid, the hydrogen-ion concentration of the mixture can be calculated if it is assumed that the sodium acetate is completely ionized (or a measured activity coefficient is used) and if it is assumed that the concentration of the acetic acid is unaffected by the slight ionization into its ions. If a solution were 0.1 M in acetic acid, and 0.2 M in sodium acetate, a rough calculation would give: $([H^+]0.2/0.1) = 1.86 \times 10^{-5}$, $[H^+] = 0.93 \times 10^{-5}$.

Buffering agents or solutions are well known and documented in the literature. They are commercially available from numerous suppliers, and the practice of the present invention is not limited to any particular buffer or buffering agent. For example, a buffer or buffering agent may be prepared as described on pp. 971, 972 of *Lange's Handbook of Chemistry* (revised 10th edition). Additionally, for purposes of illustrative examples set forth below, buffering agents were used which were made in accordance with *Chemical Rubber Co. Handbook of Chemistry and Physics*, (47th Edition), "Buffer Solutions, Properties of Standard Aqueous, at 25° C.".

The invention is further illustrated in the following examples:

EXAMPLE I

5% by volume acrolein was placed in several commercially available acidic buffer solutions. The solutions were stored at 22° C. Gas chromatography was used as the analytical method to measure the concentration of acrolein. The gas chromatogram utilized a ⅛th inch by six foot poropak Q column at 200° C., FID detectors at 250° C. and injector at 250° C., with a nitrogen flow rate of 32ml. per minute. One ml. aliquot samples were removed from the initial buffer solutions at various time intervals and mixed with 0.05 ml. purified dioxane. The resulting solution was analyzed by gas chromatography for amounts of acrolein in relation to time. The acrolein lifetime was calculated from the resulting curves. This testing procedure is further described in Brady, et al., "*Oil Field Subsurface Injection of Water*" A.S.T.M., S.T.P., Vol. 641, pp 89–108 (1977).

The test clearly indicated that the lifetime of acrolein was increased in lower pH environments, with the maximum lifetime occurring between about pH 3 and about pH 4, although quite significant and economically useful increases were obtained at pH values from between about pH 2 and about pH 6.

The test is further illustrated in the following table:

Table 1

| Composition of buffer system | pH | Lifetime of acrolein at 22° C. (days) |
|---|---|---|
| $KH_2PO_4$/NaOH | 7 | 8 |
| $KH_2PO_4$/NaOH | 6 | 10 |
| $KHC_8H_4O_4$/NaOH | 5 | 11 |
| $KHC_8H_4O_4$/HCl | 4 | 14 |
| $KH_8H_4O_4$/HCl | 3 | 18 |
| KCl/HCl | 2 | 11 |

EXAMPLE II

Five ml. acrolein was diluted at 22° C. with a 95 ml. aliquot of several commercially available buffer solutions. The analysis method was as described in E. S. Littman, "*Oilfield Bactericide Parameters as Measured by ATP Analysis*" Society of Petroleum Engineers of the A.I.M.E. Preprint No. S.P.E. 5312 (1975). This test again illustrated that lowering the pH to the acidic side will significantly enhance the lifetime of acrolein.

The results of this test are further illustrated in the following table.

Table 2

| Composition of buffer system | pH | Lifetime of acrolein at 22° C. (days) |
|---|---|---|
| $KH_2PO_4$/NaOH | 7 | 7 |
| $KH_2PO_4$/NaOH | 6 | 11 |
| $KHC_8H_4O_4$/NaOH | 5 | 14 |
| $KHC_8H_4O_4$/HCl | 4 | 17 |
| $KHC_8H_4O_4$/HCl | 3 | 19 |
| KCl/HCl | 2 | 8 |

EXAMPLE III 0.01 ml. acrolein was placed in 99.99 ml. of selected commercially available buffer solutions at 35° C. These solutions contained an initial acrolein concentration of 100 ppm. The analysis of acrolein was performed using differential pulse polarography as defined in Howe, *Analytical Chemistry*, Vol. 48, p. 2167 (1976). From 10 ml. aliquots, graphs were constructed by plotting concentration versus time, and thereby computing lifetimes. Even though a different acrolein concentration and a different temperature were used in this Example from those of Examples I and II, significant and useful increases in lifetime were obtained in the pH range from about 2 to about 6.

The results of this test are illustrated in the table below:

Table 3

| Composition of buffer system | pH | Lifetime of acrolein at 35° C. (hours) |
|---|---|---|
| KH$_2$PO$_4$/NaOH | 7 | 30 |
| KH$_2$PO$_4$/NaOH | 6 | 44 |
| KHC$_8$H$_4$O$_4$/NaOH | 5 | 56 |
| KHC$_8$H$_4$O$_4$/HCl | 4 | 86 |
| KHC$_8$H$_4$O$_4$/HCl | 3 | 120 |
| KCl/HCl | 2 | 92 |

EXAMPLE IV

Acrolein was placed in selected commercially available buffer solutions at an initial concentration of 100 ppm. at 25° C. and thereafter placed into aqueous solutions containing test bacteria. These solutions were analyzed using the testing procedure of Example II, and percent kills of aerobic bacteria were determined at various times. This test clearly illustrates that the lifetime of acrolein as determined by its biocidal potency increases with decreasing pH. Additionally, this test clearly indicates that more aerobic bacteria can be destroyed over a longer period of time using the same initial concentration of acrolein at pH 3, than can be accomplished with equal amounts of acrolein at either pH 5 or pH 7.

This is further detailed in the following table.

Table 4

| pH | Lifetime of acrolein at 35° C. (hours) |
|---|---|
| 7 | 5 |
| 5.5 | 6 |
| 4.5 | 10 |
| 3.5 | 208 |
| 2.1 | 131 |

Although the invention has been described in terms of specified embodiments which are set forth in detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A method of enhancing the effective life of acrolein in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of a buffered acid solution, whereby said aqueous medium having acrolein present therein is reduced to from between about pH 6 and about pH 2.

2. A method of enhancing the effective life of acrolein in an aqueous medium comprising the steps of: (A) adjusting the pH of the aqueous medium by contacting said medium with an effective pH-reducing amount of a buffered acid solution, whereby said aqueous medium is reduced to from between about pH 6 and about pH 2; and (2) introducing into said buffered acidic aqueous medium a predeterminable amount of acrolein.

3. A method of enhancing the effective life of acrolein in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of a buffered acid selected from the class consisting of: (1) H$_x$A$_y$, wherein H is a hydrogen, A is an inorganic radical, and x and y each are positive integers whereby H and A are valence balanced; (2) RA, wherein R is one of hydrogen, an alkyl or an aryl group, and A is one of CO$_2$H, OPO$_3$H$_2$, PO$_3$H$_2$, OSO$_3$H, and SO$_3$H; and (3)

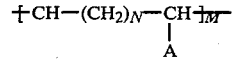

wherein N is zero or a positive integer from one through three, M is a positive integer of at least one, and A is a member selected from the class consisting of CO$_2$H, OPO$_3$H$_2$, PO$_3$H$_2$, OSO$_3$H, and SO$_3$H.

4. The method of claim 3 wherein said buffered acid is hydrochloric acid.

5. The method of claim 3 wherein said buffered acid is sulfuric acid.

6. The method of claim 3 wherein said buffered acid is acetic acid.

7. A method of enhancing the effective life of acrolein in an aqueous medium comprising the steps of: (A) adjusting the pH of the aqueous medium having acrolein present therein by contacting said medium with an effective pH-reducing amount of a buffered acid selected from the class consisting of: (1) H$_x$A$_y$, wherein H is hydrogen, A is an inorganic radical, and x and y each are positive integers whereby H and A are valence balanced; (2) RA, wherein R is one of hydrogen, an alkyl or an aryl group, and A is one of CO$_2$H, OPO$_3$H$_2$, PO$_3$H$_2$, OSO$_3$H, and SO$_3$H; and (3)

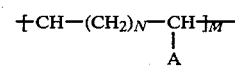

wherein N is zero or a positive integer from one through three, M is a positive integer of at least one, and A is a member selected from the class consisting of CO$_2$H, OPO$_3$H$_2$, PO$_3$H$_2$, OSO$_3$H, and SO$_3$H; and (B) introducing into said aqueous medium a predetermined amount of acrolein.

8. The method of claim 7 wherein said buffered acid is hydrochloric acid.

9. The method of claim 7 wherein said buffered acid is sulfuric acid.

10. The method of claim 7 wherein said buffered acid is acetic acid.

11. A method of enhancing the effective life of acrolein in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of a buffered acid selected from the class consisting of: (1) H$_x$A$_y$, wherein H is hydrogen, A is an inorganic radical, and x and y each are positive integers whereby H and A are valence balanced; (2) RA, wherein R is one of hydrogen, an alkyl or an aryl group, and A is one of CO$_2$H, OPO$_3$H$_2$, PO$_3$H$_2$, OSO$_3$H, and SO$_3$H; and (3)

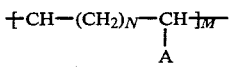

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2.

12. A method of enhancing the effective life of acrolein in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of a buffered organic acid, a buffered inorganic acid or mixtures thereof selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

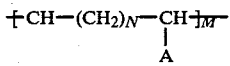

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2.

13. A method of effectively reducing aerobic, anaerobic or sulfate-reducing bacteria in an aqueous medium comprising the steps of: A introducing into said aqueous medium a predetermined amount of acrolein; (B) adjusting the pH of the aqueous medium having acrolein present therein by contacting said medium with an effective pH-reducing amount of a buffered organic acid, a buffered inorganic acid or mixtures thereof selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

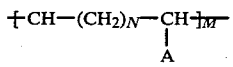

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2; and (C) contacting said aerobic, anaerobic or sulfate-reducing bacteria with an effective bacteria reducing amount of said buffered acidic aqueous medium.

14. A method of effectively reducing aerobic, anaerobic or sulfate-reducing bacteria in an aqueous medium comprising the steps of: (A) adjusting the pH of the aqueous medium by contacting said medium with an effective pH-reducing amount of a buffered organic acid, a buffered inorganic acid or mixtures thereof, selected from the class consisting of: (1) $H_xA_y$, wherein H is hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $PO_3H_2$, $OSO_3H$, and $SO_3H$; and (3)

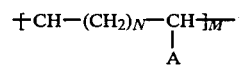

wherein N is zero or a positive integer from one through three, M is a positive integer of at least one, and A is a member selected from the class consisting of $CO_2H$, $OPO_3H_2$, $PO_3H_2$, $OSO_3H$, and $SO_3H$, said pH thereby being adjusted and reduced to between about pH 6 and about pH 2; (B) introducing into said aqueous medium a predetermined amount of acrolein; and (C) contacting said aerobic, anaerobic or sulfate-reducing bacteria with an effective bacteria-reducing amount of said buffered acidic aqueous medium.

15. A method of effectively rendering hydrogen sulfide inert in an aqueous medium comprising the steps of: (A) introducing into said aqueous medium a predetermined amount of acrolein; and (B) adjusting the pH of the aqueous medium having acrolein present therein by contacting said medium with an effective pH-reducing amount of a buffered inorganic acid, a buffered inorganic acid or mixtures thereof selected from the class consisting of: (1) $H_xA_y$, wherein H is a hydrogen, A is an inorganic radical, and x and y each are positive integers whereby H and A are valence balanced; (2) RA, wherein R is one of hydrogen, an alkyl or an aryl group, and A is one of $CO_2H$, $OPO_3H_2$, $OSO_3H$, and $SO_3H$; and (3)

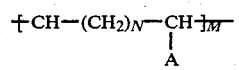

wherein N is zero or a positive integer from one through three, M is a positive integer of at least one, and A is a member selected from the class consisting of $CO_2H$, $OPO_3H$, $OSO_3H$, and A is a member selected from the class consisting of $CO_2H$, $OPO_3H_2$, $OSO_3H$, and $SO_3H$, said pH thereby being adjusted and reduced to between about pH 6 and about pH 2; and (C) contacting said hydrogen sulfide with said buffered acidic aqueous medium.

* * * * *